United States Patent [19]

Crocker et al.

[11] 4,393,230

[45] Jul. 12, 1983

[54] METHOD OF PREPARING ETHYL SILICATE

[75] Inventors: William A. Crocker, Corvallis; Duane L. Hug, Albany, both of Oreg.

[73] Assignee: Teledyne Industries, Inc., Albany, Oreg.

[21] Appl. No.: 305,554

[22] Filed: Sep. 25, 1981

[51] Int. Cl.³ .............................. C07F 7/08; C07F 7/18
[52] U.S. Cl. ...................................... 556/457; 556/458
[58] Field of Search ................................ 556/457, 458

[56] References Cited

U.S. PATENT DOCUMENTS 3,320,297  5/1967  Pino ..................................... 556/458

FOREIGN PATENT DOCUMENTS 785312  12/1980  U.S.S.R. ............................... 556/457

Primary Examiner—Paul F. Shaver
Attorney, Agent, or Firm—Shoemaker and Mattare, Ltd.

[57] ABSTRACT

A method of continuously producing in high yield ethyl silicate having a predetermined content of silica by adjusting the flowrate of reactants to the reactor in relation to the temperature of the reaction.

5 Claims, 2 Drawing Figures

RELATIONSHIP BETWEEN REACTION TEMPERATURE AND SILICA CONTENT

METHOD OF PREPARING ETHYL SILICATE

BACKGROUND OF THE INVENTION

1. Field of the Invention

This invention relates to a method of continuously producing ethyl silicate. More specifically, it deals with a method of accurately controlling the flowrate of the reactants in relation to the temperature of the reaction.

2. Description of the Prior Art

Ethyl silicate, available commerically for many years, has been used in paints and as binders in the refractory and foundry industry. The most commercial form of ethyl silicate sold and used is ethyl silicate 40, which contains 40% silica.

Ethyl silicates were first prepared batchwise by adding a predetermined quantity of liquid silicon tetrachloride to an agitated, jacketed reactor and then introducing an excess of ethyl alcohol at a controlled rate. The reactor contents were chilled to prevent the undesirable volatilization of silicon tetrachloride before reaction which lowered product yields. Hydrogen chloride gas was removed by stripping with dry air or heating and stirring the mixture.

If anhydrous ethanol is used, the reaction which produced tetraethyl orthosilicate is represented below:

$$SiCl_4 + 4C_2H_5OH \rightarrow Si(OC_2H_5)_4 + 4HCl$$

If ethanol containing some water is used, the reaction can be described as follows:

$$SiCl_4 + (4-n)C_2H_5OH + n/2H_2O \rightarrow Si(OC_2H_5)_{4-n}O_{n/2} + 4HCl$$

When n = 1.57, ethyl polysilicate containing 40% $SiO_2$ is produced, which, as set forth above, is termed ethyl silicate 40.

Partial ethanolysis of silicon tetrachloride can occur according to the following reactions:

$$SiCl_4 + C_2H_5OH \rightarrow (C_2H_5O)SiCl_3 + HCl$$

$$(C_2H_5O)SiCl_3 + C_2H_5OH \rightarrow (C_2H_5O)_2SiCl_2 + HCl$$

$$(C_2H_5O)_2SiCl_2 + C_2H_5OH \rightarrow (C_2H_5O)_3SiCl + HCl$$

$$(C_2H_5O)_3SiCl + C_2H_5OH \rightarrow Si(OC_2H_5)_4 + HCl$$

During the batch preparation of tetraethoxysilane (tetraethyl orthosilicate), several side reactions take place, including hydrogen chloride reacting with the ethanol to produce ethyl chloride and water and the excess silicon tetrachloride catalyzing a reaction which yields diethyl ether and water from ethanol:

$$C_2H_5OH + HCl \longrightarrow C_2H_5Cl + H_2O$$

$$2\ C_2H_5OH \xrightarrow{SiCl_4} C_2H_5OC_2H_5 + H_2O$$

The water produced then reacts with the silicon tetrachloride and the tetraethoxysilane product:

$$SiCl_4 + 2H_2O \rightarrow SiO_2 + 4HCl$$

$$2Si(OC_2H_5)_4 + H_2O \rightarrow (C_2H_5O)_3Si\text{-}OSi(OC_2H_5)_3 + 2C_2H_5OH$$

$$Si(OC_2H_5)_4 + 2H_2O \rightarrow SiO_2 + 4C_2H_5OH$$

When an excess of silicon tetrachloride is present, it can react with ethyl orthosilicate to give polymeric products:

$$Si(OC_2H_5)_4 + SiCl_4 \rightarrow 2(C_2H_5O)_2SiCl_2$$

In order to reduce the extent of the side reactions which lower yield and consistently produce an ethyl silicate 40 of acceptable quality, the reaction is performed continuously with steady removal of "crude" ethyl silicate 40 and evolution of hydrogen chloride gas. The crude material is purified by distillation, neutralization, and filtration to remove the undesirable excess ethanol, reaction by-products, and residual hydrogen chloride.

Although both batch and continuous processes for producing ethyl silicate have been known in the past, the accuracy of maintaining the continuous production of high yields of the precise ethyl silicate, having the desired percentages of $SiO_2$ content, has presented many problems, some of which are set forth above. There is also the problem of reliance on the accuracy of the two flow meters, one in harsh silicon tetrachloride service, plus the careful storage of the ethanol solution to prevent moisture absorption. There is, therefore, a need for a more accurate control for producing high yields of ethyl silicate having predetermined amounts of $SiO_2$.

BRIEF SUMMARY OF THE INVENTION

It is, accordingly, one object of the present invention to provide a new process for accurately controlling the flowrate of the reactants for the production of ethyl silicate so as to produce ethyl silicate having predetermined amounts of $SiO_2$ content.

Another object of the present invention is to provide a new process for the production of ethyl silicate wherein not all of the reactants require adjustment of their flowrates during the process.

A more precise object of the present invention is to control the flowrate of the ethanol and water mixture in relation to the temperature of the reactor wherein ethyl silicate 40 is produced.

These and other advantages of the present invention will be apparent from the detailed description and drawings.

FIG. 1 discloses a schematic apparatus for producing ethyl silicate; and

FIG. 2 is a graph showing the relationship between temperature and silica content.

In accordance with the above objects, it has been found that ethyl silicate, having a predetermined percentage of $SiO_2$, can be produced in high yields when the reaction is maintained at a certain temperature. By predetermined amounts of $SiO_2$ is meant within the range of the reaction wherein water is one of the reactants, which produces a product which contains about 28.8% $SiO_2$, up to that amount where $SiO_2$ is precipitated out of solution (about 53% $SiO_2$ content). By controlling the flowrate of the reactants in relation to temperature changes, it is possible to maintain a continuous process which will produce high yields of the specifically desired ethyl silicate, i.e., ethyl silicate 40. Prior art methods require an analysis technique of the product to determine the amount of silica in the reactant product. This analysis did not lend itself to a fast determination which would maintain a stabilized continuous process avoiding side reactions.

DETAILED DESCRIPTION OF THE INVENTION

This invention involves the continuous preparation of ethyl silicate having a predetermined percentage of $SiO_2$ although for purposes of illustration ethyl silicate 40 (ethyl polysilicate containing approximately 40% $SiO_2$ equivalent) is set forth as the desired product since it is the most commercial product. Liquid silicon tetrachloride and an ethanol/water mixture are continuously metered into a stirred reactor to prepare ethyl silicate 40. Since it is important to obtain a product containing between 40 and 41% $SiO_2$ by weight, the reactant feedrates are controlled to maintain a particular reactor temperature which establishes the desired silica content.

This invention involves the control of silica content during the continuous preparation of ethyl silicate 40 by maintaining a silicon tetrachloride to ethanol/water feedrate ratio which establishes the desired reactor temperature.

Figure 1:
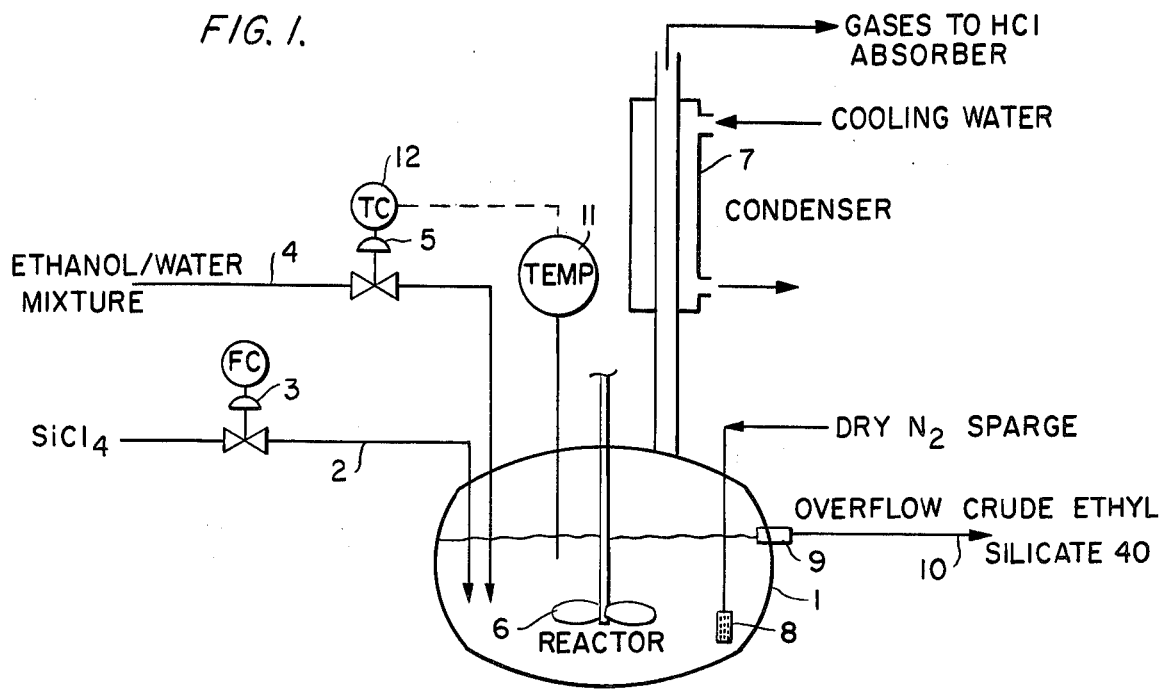

FIG. 1 shows an apparatus utilized for ethyl silicate manufacture. In this figure, liquid silicon tetrachloride is continuously introduced to the stirred reactor 1 at a controlled feedrate by means of line 2 and control valve 3. An ethanol/water mixture is continuously introduced to the stirred reactor 1 at a controlled feedrate by means of line 4 and control valve 5. The reactants are added in close proximity to each other near the agitator 6 in order to promote their reaction and prevent the escape of unreacted vapors which reduces the product yield. The reaction temperature is controlled by the ratio of the reactant feedrates, which, in turn, establishes the silica content of the crude ethyl silicate product.

The hydrogen chloride gas generated during the reaction passes through the water-cooled condenser 7 and is treated in a hydrochloric acid absorber (not shown). Dry nitrogen or air is sparged into the reaction mass by means of sparger 8 to assist in removing the hydrogen chloride which can promote undesirable side reactions and reduce product yield.

After a suitably-long reactor residence time, the crude ethyl silicate overflows the reactor by means of outlet 9 and is carried by means of conduit 10 for further treatment as follows.

Excess ethanol and undesirable by-products, including hydrogen chloride, diethyl ether, and ethyl chloride, are removed by distillation at above 105° C. The ethyl silicate bottoms are then neutralized with anhydrous ammonia to remove residual acidity consisting primarily of chlorine-containing silicon esters such as $Si(OC_2H_5)_3Cl$. The liquid is back-sparged with dry nitrogen to strip out the excess dissolved ammonia gas, and the resulting ammonium chloride particulate is filtered to yield a neutral, solids-free, water-clear ethyl silicate containing, in this case, between 40 and 41% silica by weight.

Temperature Gauge 11 measures the temperature of the reaction which is relayed to temperature control device 12 which continuously adjusts the flowrate of the ethanol/water mixture to the reactor in response thereto by means of valve 5.

In the continuous production of ethyl silicate, an excess of ethanol is introduced to ensure complete reaction with the silicon tetrachloride. The silica concentration in the product is established by the amount of water added to the reactor with the ethanol. Therefore, to carefully control the silica content during current commercial production, the amount of water contained in the ethanol, as well as the flow ratio of silicon tetrachloride to ethanol-water solution, must be precisely known and controlled in order to obtain consistent product.

With this new process, an ethanol-water mixture of a certain composition is prepared, and the ethyl silicate reaction is commenced by adding the reactants at predetermined flowrates. Once the reaction has reached steady-state conditions, the silica composition of the product can be established at a specified level, i.e., near 40% by controlling the feed ratio to maintain the desired reactor temperature. Since temperature is an easy and accurate measurement commonly used in the chemical process industry, continuous reaction control is relatively simple.

The silicon tetrachloride flowrate can be fixed and the ethanol-water flowrate can be automatically controlled to maintain the desired temperature and, therefore, the desired silica concentration. Basically, the flowrate of any of the reactants can be set and one of them adjusted constantly in relation to temperature changes. It is necessary to keep in mind that as the ratio of silicon tetrachloride to the ethanol-water mixture goes up, the temperature goes down. Therefore, as set forth in the illustration in the present case, the silicon tetrachloride flowrate is set and the ethanol-water mixture is adjusted upward to increase the temperature in the reactor and downward to decrease the temperature in the reactor.

With the method of the present invention, it does not matter even when there are fluctuations in the flowrate of the fixed reactants since the one adjustment of one of the reactants will accommodate these changes to constantly produce a stable product. Therefore, changes due to leaky valves or rust or some other physical deficiency will be obviated.

Three examples were conducted to demonstrate this new concept for controlling silica content.

EXAMPLE 1

A continuous experiment to produce ethyl silicate 40 was conducted for approximately 90 minutes. 2642 grams of refined silicon tetrachloride and 2462 grams of ethanol solution containing 9.2% water by weight were continuously added to a stirred reactor. The reaction temperature was maintained at 42°–43° C., the condenser temperature was 10° C., and the calculated reactor residence time was approximately 9 minutes. About 31% more ethanol than stoichiometrically required was introduced, and the ethyl silicate was analyzed to contain 43.6% $SiO_2$ after distillation, neutralization, sparging, and filtration.

EXAMPLE 2

Later in time when it was suspected that the silica content of the product could be controlled by the reaction temperature which was established by the flow ratio of silicon tetrachloride to ethanol-water, another continuous experiment to produce ethyl silicate 40 was conducted for 15 hours and 36 minutes. 29.06 kg of silicon tetrachloride and 22.17 kg of ethanol solution containing 11.2% water by weight were continuously added to the stirred reactor. The reaction temperature was maintained at an average of 27° C., the condenser temperature was 13°–14° C., and the calculated residence time was 10.7 minutes. About 5% more ethanol than stoichiometrically required was introduced, and the ethyl silicate was analyzed to contain 39.4% SiO$_2$ after distillation, neutralization, sparging, and filtration.

EXAMPLE 3

With the results of Examples 1 and 2, it could now be predicted that in order to obtain ethyl silicate containing between 40 and 41% SiO$_2$, a reaction temperature just slightly above 30° C. must be maintained. A continuous experiment to prepare ethyl silicate 40 was conducted for 14 hours and 1 minute. 21.03 kg of silicon tetrachloride and 17.11 kg of ethanol solution containing 11.2% water by weight were continuously added to the stirred reactor. The reaction temperature was maintained at 32° C., the condenser temperature was 12°–14° C., and the calculated reactor residence time was approximately 12.4 minutes. About 12% more ethanol than stoichiometrically required was introduced, and the ethyl silicate was analyzed after further treatment to contain 40.4% SiO$_2$, as predicted.

Figure 2:
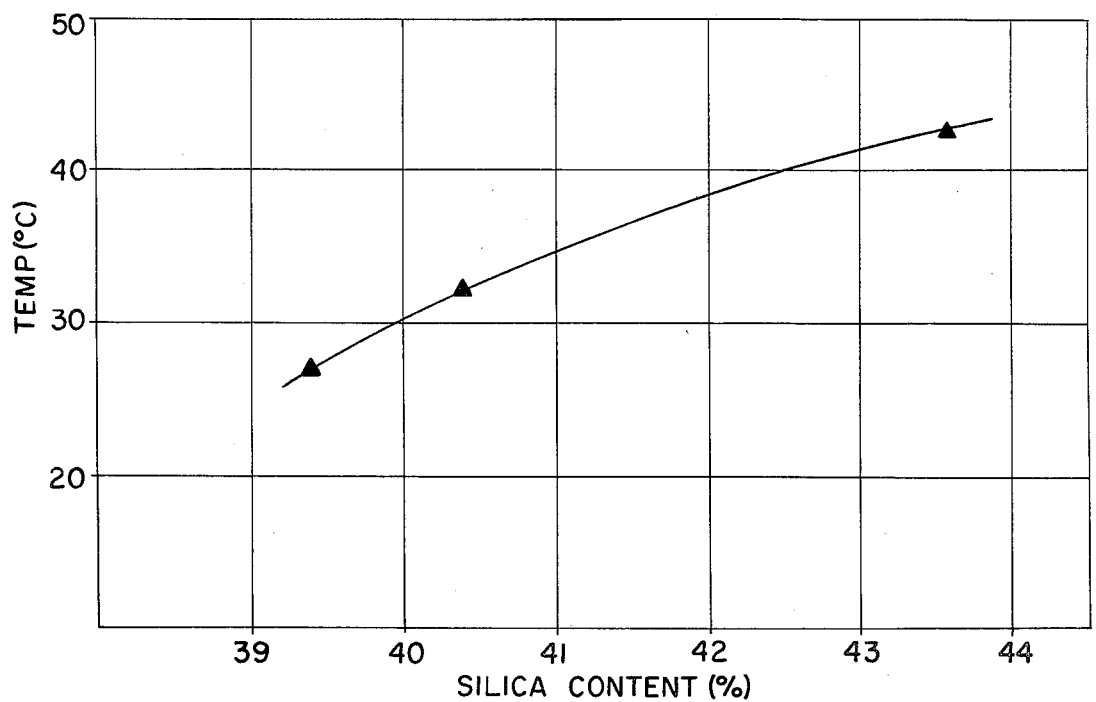

The results of the above examples are tabulated in Table I and graphically set forth in FIG. 2.

TABLE I

| Exp. | Water in Ethanol | Excess Ethanol | Reaction Temperature | Calculated Residence Time | Final SiO$_2$ Composition |
| --- | --- | --- | --- | --- | --- |
| #1 | 9.2% | 31% | 42–43° C. | 9 min | 43.6% |
| #2 | 11.2 | 5 | 27 | 10.7 | 39.4 |
| #3 | 11.2 | 12 | 32 | 12.4 | 40.4 |

As set forth above, ethyl silicate having a predetermined amount of silica content can be made in high yields continuously by maintaining the temperature of the reactor at the desired level for the particular product by adjusting the flow of the reactants in relation to fluctuations in temperature.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalent are, therefore, intended to be embraced by those claims.

We claim:

1. A method of continuously producing ethyl silicate, having a predetermined percentage of silica content, in high yields from the reactants silicon tetrachloride, ethanol and water comprising adjusting the flowrate of the reactants to the reactor in relation to fluctuations in the temperature of the reaction in the reactor.

2. The process of claim 1 wherein the silica content of the ethyl silicate is between 28.8 and 53% by weight of the ethyl silicate.

3. The method of claim 1 wherein the flowrate of the silicon tetrachloride is set, the ratio of ethanol to water is set and the flowrate of only the ethanol-water mixture is adjusted in relation to changes in temperature in the reactor.

4. The process of claim 3 wherein the flowrate of the ethanol-water mixture is set and the flowrate of the silicon tetrachloride is adjusted in relation to changes in temperature in the reactor.

5. The process of claim 1 wherein the ethyl silicate produced has a silica content of 40% by weight of the ethyl silicate and the temperature of the reaction is maintained at about 30° C. by adjusting the flowrate of the reactants.

* * * * *